United States Patent [19]

Abou-Gharbia

[11] Patent Number: 4,636,563
[45] Date of Patent: Jan. 13, 1987

[54] ANTIPSYCHOTIC γ-CARBOLINES

[75] Inventor: Magid A. Abou-Gharbia, Wilmington, Del.

[73] Assignee: American Home Products Corporation, New York, N.Y.

[21] Appl. No.: 776,180

[22] Filed: Sep. 16, 1985

[51] Int. Cl.[4] .................. C07D 471/04; C07D 401/02; C07D 241/36

[52] U.S. Cl. ........................................ 546/87; 546/86; 544/405; 544/353

[58] Field of Search .................... 546/87, 86; 544/405, 544/353, 354

[56] References Cited

U.S. PATENT DOCUMENTS

| | | | |
|---|---|---|---|
| 3,502,688 | 3/1970 | Berger et al. | 546/86 |
| 3,522,262 | 7/1970 | Berger et al. | 546/86 |
| 4,001,263 | 1/1977 | Plattner et al. | 546/85 |
| 4,224,329 | 9/1980 | Welch, Jr. | 546/85 |

Primary Examiner—Henry R. Jiles
Assistant Examiner—J. Richter
Attorney, Agent, or Firm—Richard K. Jackson

[57] ABSTRACT

The compounds:

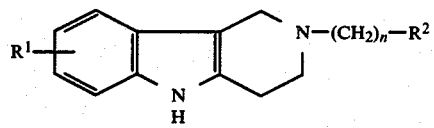

in which
  $R^1$ is hydrogen, halogen, hydroxy, or alkyl;
  $R^2$ is substituted or unsubstituted pyridinyl, pyrazinyl, quinolinyl or quinoxalinyl and said substituents are alkyl, alkoxy, alkoxycarbonyl, halogen, cyano or nitro; and
  n is 2, 3, 4, 5 or 6;
or a pharmaceutically acceptable salt thereof, are antipsychotic and anxiolytic agents.

15 Claims, No Drawings

ANTIPSYCHOTIC γ-CARBOLINES

BACKGROUND OF THE INVENTION

Gamma-carbolines possessing central nervous system activity are known. Representative of the compounds found in the literature are those disclosed by Plattner et al., U.S. Pat. No. 4,001,263 and Welch, U.S. Pat. No. 4,224,329 as 2-substituted-5-aryl-tetra-and hexahydro-pyrido[4,3-b]indoles. Each reference discloses preferred phenyl(oxy or oxo)alkyl substitution in 2-position.

DESCRIPTION OF THE INVENTION

In accordance with this invention there is provided a group of tetrahydro-2-heterocycloalkyl-pyrido[4,3-b]indoles which possess antipsychotic and anxiolytic properties useful in the treatment of psychological disorders such as paranoia and schizophrenia and states of anxiety.

The compounds of this invention present the structural formula:

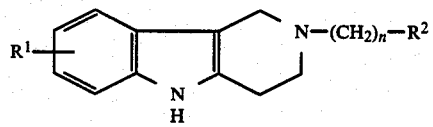

in which
$R^1$ is hydrogen, halogen, hydroxy or alkyl of 1 to 6 carbon atoms;
$R^2$ is

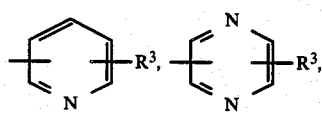

where $R^3$ is hydrogen, alkyl of 1 to 6 carbon atoms, alkoxy of 1 to 6 carbon atoms, —$CO_2R^4$ where $R^4$ is alkyl of 1 to 6 carbon atoms, halogen, cyano or nitro; and
n is one of the integers 2, 3, 4, 5 or 6;
or a pharmaceutically acceptable salt thereof.

Preferred among the compounds embraced by the foregoing genus are those of the formula:

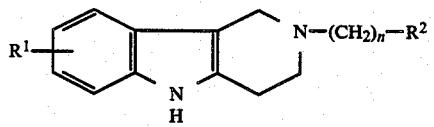

in which
$R^1$ is hydrogen or halogen;
$R^2$ is

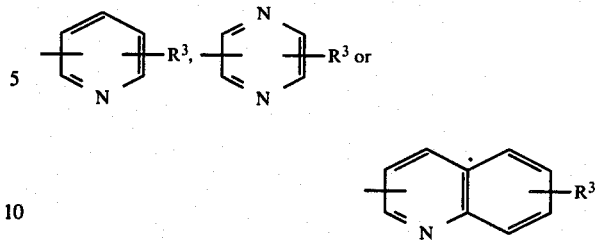

where $R^3$ is hydrogen, alkyl of 1 to 4 carbon atoms, alkoxy of 1 to 4 carbon atoms, —$CO_2R^4$ where $R^4$ is alkyl of 1 to 4 carbon atoms, halogen, cyano or nitro; and
n is one of the integers 2, 3 or 4;
or a pharmaceutically acceptable salt thereof.

In the preceding descriptions of the compounds of this invention, the term, "halogen" is intended to embrace chlorine, bromine and fluorine and the pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The compounds of this invention are readily prepared by a variety of conventional methods generally involving alkylation at 2-position of an appropriately substituted gamma-carboline. For example, in Scheme 1, an appropriately substituted γ-carboline II may be reacted with either haloalkylpyridine, haloalkylpyrazine, haloalkylquinoline or haloalkylquinoxaline III (route 1a) or a vinylpyridine, vinylpyrazine, vinylquinoline or vinylquinoxaline IV, (route 1b) in which $R^1$ and $R^2$ are as previously defined.

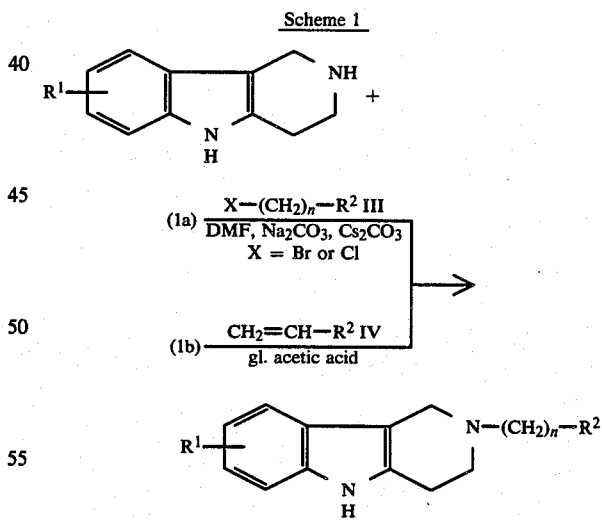

Scheme 1

The nucleophilic substitution reaction (1a) is run in an aprotic solvent, such as dimethylformamide (DMF), dimethylsulfoxide (DMSO), acetone or alcoholic acetonitrile in the presence of a mild base such as sodium, potassium or cesium carbonate or a combination of two different carbonates.

The vinyl Michael addition reaction (1b) may be used where compounds of the invention having n=2 are desired. The reactions are conveniently run in an alcoholic solvent, preferably methanol or ethanol, in the presence of a catalytic amount of glacial acetic acid. These reactions are preferably run at solvent reflux temperatures for 24–48 hours.

The starting γ-carboline II in Scheme 1 (above) are prepared from substituted phenylhydrazines and N-carbethoxy-4-piperidone as shown in Scheme 2.

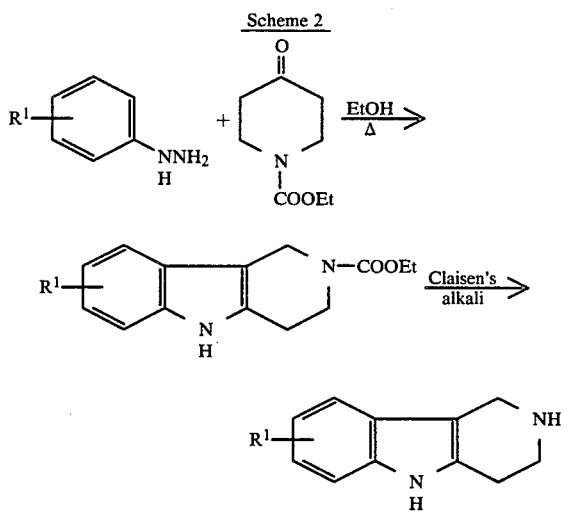

The antipsychotic properties of the compounds of this invention were established by standard pharmacologically accepted procedures involving two conditioned avoidance studies in which trained male CD rats (Charles River), 400–450 gm body weight are exposed to a fifteen second warning tone (conditioned stimulus) continued for an additional fifteen seconds accompanied by electric shock. The rat can avoid the electric shock by depression of a response lever (lever-response) or in a different study by jumping to an exposed shelf (shelf-jump response). In either test situation, a response during the initial warning tone is considered an avoidance response while a response during shock delivery is considered an escape response. The avoidance response is determined and expressed as a percentage of total trials from an appropriate number of trials and a 50% block in avoidance responding ($AB_{50}$) is obtained from a dose-effect regression line. The shelf-jump response test procedure follows that of Herman et al., Comm. in Psychopharm., 3, pp. 165–171 (1979).

As a measure of extrapyramidal side effects, the compounds of this invention were studied as antagonists of apomorphine-induced stereotyped behavior wherein CF-1 mice (Charles River) receive the test compound i.p. (six mice per dose level) and thirty minutes later receive 10 mg/kg apomorphine s.c. Five minutes after injection, the rearing-head-bobbing-licking syndrome induced by apomorphine is evaluated as present or absent for each animal. Readings are repeated every five minutes during a thirty minute test session. An $ED_{50}$ value (with 95% confidence intervals) is calculated for inhibition of apomorphine-induced stereotyped behavior by simple linear regression analysis. The compounds of this invention were inactive in this study, demonstrating a low potential for side-effects attending long term treatment with such standard antipsychotic drugs as haloperidol and chlorpromazine.

In further support of the low potential for side-effects exhibited by the compounds of this invention, the compounds were tested in accordance with a modification of the procedure of Fields et al., Brain Res., 136, pp. 578–584 (1977) and Yamamura et al., eds., Neurotransmitter Receptor Binding, Raven Press, N.Y. (1978), wherein homogenized limbic brain tissue is incubated with $^3$H-spiroperidol and various concentrations of test compound, filtered and washed and shaken with Hydrofluor scintillation cocktail (National Diagnostics) and counted in a Packard 460CD sintillation counter. Binding in the presence of the test compound is expressed as a percent of specific binding (total binding less binding in the presence of 1 μM (+)butaclamol). An inhibition constant ($K_i$) is calculated for each test compound to catagorize its limbic D-2 binding potential. The larger the number, the less potential for dopamine receptor binding and attendant side effects from administration of the antipsychotic agent. Inhibition constants (95% confidence interval) for standard antipsychotics are:

haloperidol—4.0(3.0–5.6)nM;
clozapine—34(23–54)nM;
fluphenazine—4.5(3.6–5.6)nM; and
sulpiride—376(174–5000)nM In an analogous test procedure employing brain cortical tissue, the compounds of this invention which have been tested demonstrated an equal or greater potency than serotonin for binding at serotonin-2 receptors. Serotonin exhibits a $K_i$ in this study of 20 (14–30) μM while dopamine is inactive.

From these data, the activity profile of the compounds of this invention are seen to be that of antipsychotic agents with much lower potential for extra pyramidal side effects such as attend the use of major tranquillizers (sedation, pseudoparkinsonism, ataxia, muscle relaxation, etc.). This activity profile resembles that of the anxiolytic compound, buspirone.

Hence, the compounds of this invention are antipsychotic agents and anxiolytic agents useful in the treatment of psychoses such as paranoia and schizophrenia and in alleviating anxiety. As such, they may be administered neat or with a pharmaceutical carrier to a patient in need thereof. The pharmaceutical carrier may be solid or liquid.

A solid carrier can include one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and sized desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both of pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g.. glycols) and their derivatives, and oils (e.g. fractionated coconut oil and arachis oil). For parenteral administration the carrier can also be an oil ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or table itself, or it can be the appropriate number of any such compositions in package form.

The dosage to be used in the treatment of a specific psychosis must be subjectively determined by the attending physician. The variables involved include the specific psychosis or state of anxiety and the size, age and response pattern of the patient.

The following examples illustrate the production of compounds of this invention. After each example the pharmacological evaluation for the compound produced is presented. The conditioned avoidance tests are reported as relative activity for the shelf-jump (S-J) at the intraperitoneal (i.p.) dose administered in mg/kg and the $AB_{50}$ is presented for the lever-response (L-R) test at the oral (p.o.) dose in mg/kg. The inhibition constant is reported for limbic D-2 binding expressed in nM concentration. Similarly, the inhibition constant for cortical 5-$HT_2$ binding is reported as the inhibition constant in nM concentration. All of the compounds were inactive as apomorphine antagonists.

EXAMPLE 1

8-Fluoro-2,3,4,5-tetrahydro-2-[4-(4-pyridinyl)butyl]-1H-pyrido[4,3-b]-indole

To a stirred suspension of 8-fluoro-2,3,4,5-tetrahydro-1H-pyrido[4,3-b]indole (1.5 g, 0.0079 mol), freshly baked anhydrous sodium carbonate (1.7 g, 0.016 mol) and catalytic amount of cesium carbonate in 70 mL of dimethylformamide, was added 2.33 g (0.016 mol) of 4-pyridinylbutyl bromide hydrobromide.

The reaction was stirred overnight at room temperature, then the solvent was removed under vacuum and the solid cake was suspended in 100 mL of water and extracted with methylene chloride (3×100 mL).

The methylene chloride extracts were combined, dried over anhydrous sodium sulfate and evaporated under reduced pressure. The title compound was separated by HPLC using ethyl acetate as the eluent to afford 2.3 g (92% yield) of the title compound which was converted to the dihydrochloride salt; mp 210°–212° C.

Analysis for: $C_{20}H_{22}N_3F.2HCl.H_2O$: Calculated: C, 57.97; H, 6.3; N, 10.14; Found: C, 57.67; H, 5.78; N, 10.29.

S-J Active (20)
L-R 15.11 (p.o. (10.38–34.33)
Limbic D-2 143 (92–214)
Cortical 5-$HT_2$ 480 (140–980)

EXAMPLE 2

8-Fluoro-2,3,4,5-tetrahydro-2-[2-(2-pyridinyl)ethyl]-1H-pyrido[4,3-b]indole

A mixture of 8-fluoro-2,3,4,5-tetrahydro-1H-pyrido[4,3-b]indole 3.2 g (0.016 mol), 2-vinylpyridine (1.79 g, 0.017 mol), and 2 mL of glacial acetic acid were refluxed for 48 hours in 30 mL of methanol. The solvent was removed in vacuo and the separated solid was purified by HPLC and converted to the dihydrochloride salt to afford 2.5 g (38% yield) of the title compound; mp 199°–201° C.

Analysis for; $C_{18}H_{18}N_3F.2HCl.H_2O$: Calculated: C, 55.96; H, 5.7; N, 10.88; Found: C, 56.51; H, 5.39; N, 10.96.

S-J Active (20)
L-R 37.64 p.o. (20.86–322.08)
Limbic D-2 26(13–42)
Cortical 5-$HT_2$ 173(139–220)

EXAMPLE 3

2,3,4,5-Tetrahydro-2-[2-(2-pyridinyl)ethyl]-1H-pyridol[4,3-b]indole

The title compound was prepared following the procedure of Example 2 with the exception that 2,3,4,5-tetrahydro-1H-pyrido[4,3-b]indole was used instead of 8-fluoro-2,3,4,5-tetrahydro-1H-pyrido[4,3-b]indole. The product converted to the dihydrochloride salt; mp. 189°–191° C.

Analysis for: $C_{18}H_{19}N_3.2HCl.1/2H_2O$: Calculated: C, 57.29; H, 6.4; N, 11.13, Cl, 18.79; Found: C, 57.4; H, 6.36; N, 10.97; Cl, 18.95.

S-H Activity (40)
L-R Very weak (40 p.o.)
Limbic D-2 33% at 1 μM

EXAMPLE 4

8-Fluoro-2,3,4,5-tetrahydro-2-[2-(2-quinolinyl)ethyl]-1H-pyrido[4-3-b]indole

The title compound was prepared following the procedure of Example 2 with the exception that 2-vinylquinoline was used instead of 2-vinylpyridine. The product was converted to the dihydrochloride salt; mp 192°–194° C.

Analysis for: $C_{22}H_{20}N_3F.2HCL$: Calculated: C, 62.63; H, 5.45; N, 9.96; Found: C, 62.57; H, 5.30; N, 9.43.

S-J Active (20)
Limbic D-2 185 (no C.I.)

EXAMPLE 5

2,3,4,5-Tetrahydro-2-[2-(2-quinolinyl)ethyl]-1H-pyrido[4,3-b]indole

The title compound was prepared following the procedure of Example 2 with the exception that 2,3,4,5-tetrahydro-1H-pyrido[4,3-b]indole was used instead of 8-fluoro-2,3,4,5-tetrahydro-1H-pyrido[4,3-b]indole and 2-vinylquinoline replaced 2-vinylpyridine. The product was converted to the dihydrochloride; mp 195°–197° C.

Analysis for: $C_{22}H_{21}B_3.2HCl.1 1/2 H_2O$: Calculated: C, 61.83; H, 6.13; N, 9.83, Cl, 16.6;
Found: C, 62.24; H, 5.89; N, 9.59; Cl, 16.12.
S-J Active (40)
L-R Weak (40 p.o.)
Limbic D-2 331 (238–410)

EXAMPLE 6

2,3,4,5-Tetrahydro-2-[4-(4-pyridinyl)butyl]-1H-pyrido[4,3-b]indole

The title compound was prepared following the procedure of Example 1 with the exception 2,3,4,5-tetrahydro-1H-pyrido[4,3-b]indole was used instead of 8-fluoro-2,3,4,5-tetrahydro-1H-pyrido[4,3-b]indole. The product was converted to the dihydrochloride salt; mp 204°–206° C.

Analysis for: $C_{20}H_{23}N_3.2HCl.H_2O$: Calculated: C, 60.60; H, 6.80; N, 10.60; Found: C, 60.87; H, 6.79; N, 10.62.
S-J Active (20,40)
L-R>20 p.o.
Limbic D-2 41% at 1 μM

EXAMPLE 7

2,3,4,5-Tetrahydro-2-[3-(3-pyridinyl)propyl]-1H-pyrido[4,3-b]indole

The title compound was prepared following the procedure of Example 1 with the exception 2,3,4,5-tetrahydro-1H-pyrido[4,3-b]indole was used instead of 8-fluoro-2,3,4,5-tetrahydro-1H-pyrido[4,3-b]indole and 3-pyridinylpropyl bromide hydrobromide replaced the 4-pyridinylbutyl bromide salt. The product was converted to the dihydrochloride salt; mp 223°–225° C.

Analysis for; $C_{19}H_{21}N_3.2HCl.H_2O$: Calculated: C, 59.68; H, 6.54; N, 10.99, Cl, 18.58; Found: C, 60.78; H, 6.26; N, 11.08; Cl, 18.80.
S-J Active (40)
L-R 33.09 p.o (25.58–50.65)
Limbic D-2 43% at 1 μM
Cortical 5-Ht$_2$ 252 (197–341)

EXAMPLE 8

8-Chloro-2,3,4,5-tetrahydro-2-[4-(4-pyridinyl)butyl]-1H-pyrido[4,3-b]indole

The title compound was prepared following the procedure of Example 1 with the exception that 8-chloro-2,3,4,5-tetrahydro-1H-pyrido[4,3-b]indole was used instead of 8-fluoro-2,3,4,5-tetrahydro-1H-pyrido[4,3-b]indole. The product was converted to the dihydrochloride salt; mp 227°–228° C.

Analysis for: $C_{20}H_{22}ClN_3.2HCl.H_2O$: Calculated: C, 55.74; H, 6.03; N, 9.75; Found: C, 55.74; H, 5.86; N. 9.61.
S-J Active (40)
L-R 36.08 p.o. (21.51–59.35)
Limbic D-2 106 (26–263)
Cortical 5-HT$_2$ 60 (29–132)

EXAMPLE 9

8-Chloro-2,3,4,5-tetrahydro-2-[2-(2-pyridinyl)ethyl]-1H-pyrido[4,3-b]indole

The title compound was prepared following the procedure of Example 2 with the exception that 8-chloro-2,3,4,5-tetrahydro-1-H-pyrido[4,3-b]indole was used instead of 8-fluoro-2,3,4,5-tetrahydro-1H-pyrido[4,3-b]indole. The product was converted to the dihydrochloride salt; mp. 198°–200° C.

Analysis for: $C_{20}H_{22}ClN_3.2HCl.H_2O$: Calculated: C, 53.67; H, 5.5: N, 10.43; Found: C, 53.32; H, 5.3; N, 10.21.
S-J Active (40)
L-R>40 p.o.
Limbic D-2 103 (72–141)

EXAMPLE 10

8-Chloro-2,3,4,5-tetrahydro-2-[2-(2-quinolinyl)ethyl]-1H-pyrido-[4,3-b]indole

The title compound was prepared following the procedure of Example 2 with the exception that 8-chloro-2,3,4,5-tetrahydro-1H-pyrido[4,3-b]indole was used instead of 8-fluoro-2,3,4,5-tetrahydro-1H-pyrido[4,3-b]indole and 2-vinylquinoline was used instead of 2-vinylpyridine. The product was converted to the dihydrochloride salt; mp 187°–190° C.

Analysis for: $C_{22}H_{20}ClN_3.2HCl.H_2O$:
Calculated: C, 58.37; H, 5.19; N, 9.27; Found: C, 58.34; H, 5.30; N, 9.29.
S-J Active (40)
L-R>40 p.o.
Limbic D-2 82 (47–136)

EXAMPLE 11

8-Fluoro-2,3,4,5-tetrahydro-2-[3-(3-pyridinyl)-propyl]1H-pyrido[4,3-b]indole

The title compound was prepared following the procedure of Example 1 with the exception that 3-pyridinylpropyl bromide hydrobromide was used instead of 4-pyridinylbutyl bromide hydrobromide. The product was converted to the dihydrochloride salt; mp. 215°–218° C.

Analysis for: $C_{19}H_{20}FN_3.HCl.1\frac{1}{2} H_2O$: Calculated: C, 55.74; H, 6.11; N, 10.26; Found: C, 56.06; H, 5.60; N, 10.51.
S-J Active (20)
L-R 14.42 p.o. (9.94–30.74)
Limbic D-2 395 (165–848)
Cortical 5-HT$_2$ 136 (76–299)

EXAMPLE 12

8-Chloro-2,3,4,5-tetrahydro-2-[3-(2-pyridinyl)-propyl]-1H-pyrido[4,3-b]indole

The title compound was prepared following the procedure of Example 1 with the exception that 3-pyridinylpropyl bromide hydrobromide was used instead of 4-pyridinylbutyl bromide hydrobromide and 8-chloro-2,3,4,5-tetrahydro-1H-pyrido[4,3-b]indole was used instead of 8-fluoro-2,3,4,5-tetrahydro-1H-pyrido[4,3-b]indole. The product as converted to the dihydrochloride salt; mp. 240°–242° C.

Analysis for: $C_{19}H_{20}ClN_3.2HCl$: Calculated: C, 57.22; H, 5.56; N, 10.54;
Found: C, 57.60; H, 5.49; N, 10.68.
S-J Active (40 i.p.)
L-R>40 p.o.
Limbic D-2 126 (85–183)
Cortical 5-HT$_2$ 28 (12–66)

EXAMPLE 3

8-Fluoro-2,3,4,5-tetrahydro-2-[2-(4-pyridinyl)ethyl]1H-pyrido[4,3-b]indole

The title compound was prepared following the procedure of Example 2 with the exception 4-vinylpyridine was used instead of 2-vinylpyridine. The product was converted to the dihydrochloride salt; mp. 233°-235° C.

Analysis for: $C_{18}FN_3.2HCl$: Calculated: C, 58.69; H, 5.43: N, 11.41; Found: C, 58.55; H, 5.42; N, 11.18.

S-J Active (40 i.p.)
L-R 22.85 (11.34–80.89)
Limbic D2 110 (39–274)
Cortical 5-HT$_2$ 211 (165–263)

What is claimed is:

1. A compound of the formula:

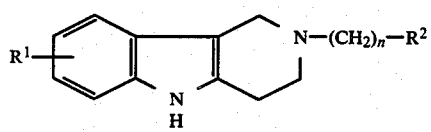

in which
R$^1$ is hydrogen, halogen, hydroxy or alkyl of 1 to 6 carbon atoms;
R$^2$ is

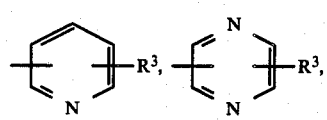

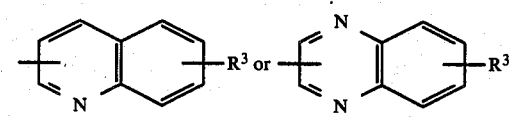

where R$^3$ is hydrogen, alkyl of 1 to 4 carbon atoms, alkoxy of 1 to 4 carbon atoms, —CO$_2$R$^4$ where R$^4$ is alkyl of 1 to 4 carbon atoms, halogen, cyano or nitro; and
n is one of the integers 2, 3, 4, 5 or 6;
or a pharmaceutically acceptable salt thereof.

2. A compound of claim 1 of the formula

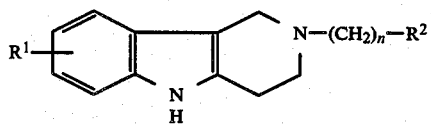

in which
R$^1$ is hydrogen or halogen;
R$^2$ is

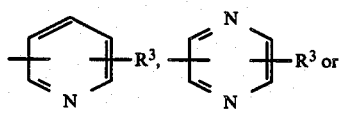

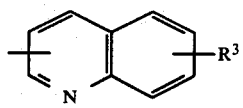

where R$^3$ is hydrogen, alkyl of 1 to 4 carbon atoms, alkoxy of 1 to 4 carbon atoms; —CO$_2$R$^4$ where R$^4$ is alkyl of 1 to 4 carbon atoms, halogen, cyano or nitro; and
n is one of the integers 2, 3 or 4;
or a pharmaceutically acceptable salt thereof.

3. The compound of claim 1 which is 8-fluoro-2,3,4,5-tetrahydro-2-[4-(4-pyridinyl)butyl]-1H-pyrido[4,3-b]indole or a pharmaceutically acceptable salt thereof.

4. The compound of claim 1 which is 8-fluoro-2,3,4,5-tetrahydro-2-[2-(2-pyridinyl)ethy]-1H-pyrido[4,3-b]indole or a pharmaceutically acceptable salt thereof.

5. The compound of claim 1 which is 2,3,4,5-tetrahydro-2-[2-(2-pyridinyl)ethyl]-1H-pyrido[4,3-b]indole or a pharmaceutically acceptable salt thereof.

6. The compound of claim 1 which is 8-fluoro-2,3,4,5-tetrahydro-2-[2-(2-quinolinyl)ethyl]-1H-pyrido[4,3-b]indole or a pharmaceutically acceptable salt thereof.

7. The compound of claim 1 which is 2,3,4,5-tetrahydro-2-[2-(2-quinolinyl)ethyl]-1H-pyrido[4,3-b]indole or a pharmaceutically acceptable salt thereof.

8. The compound of claim 1 which is 2,3,4,5-tetrahydro-2-[4-(4-pyridinyl)butyl]-1H-pyrido[4,3-b]indole or a pharmaceutically acceptable salt thereof.

9. The compound of claim 1 which is 2,3,4,5-tetrahydro-2-[3-(3-pyridinyl)propyl]-1H-pyrido[4,3-b]indole or a pharmaceutically acceptable salt thereof.

10. The compound of claim 1 which is 8-chloro-2,3,4,5-tetrahydro-2-[4-(4-pyridinyl)butyl]-1H-pyrido] indole or a pharmaceutically acceptable salt thereof.

11. The compound of claim 1 which is 8-chloro-2,3,4,5-tetrahydro-2-[2-pyridinyl)ethyl]-1H-pyrido[4,3-b]indole or a pharmaceutically acceptable salt thereof.

12. The compound of claim 1 which is 8-chloro-2,3,4,5-tetrahydro-2-[2-(2-quinolinyl)ethyl]-1H-pyrido-[4,3-b]indole or a pharmaceutically acceptable salt thereof.

13. The compound of claim 1 which is 8-fluoro-2,3,4,5-tetrahydro-2-[3-(3-pyridinyl)propyl]1H-pyrido[4,3-b]indole or a pharmaceutically acceptable salt thereof.

14. The compound of claim 1 which is 8-chloro-2,3,4,5-tetrahydro-2-[3-(2-pyridinyl)-propyl]-1H-pyrido[4,3-b]indole or a pharmaceutically acceptable salt thereof.

15. The compound of claim 1 which is 8-fluoro-2,3,4,5-tetrahydro-2-[2-(4-pyridinyl)ethyl]1H-pyrido[4,3-b]indole or pharmaceutically acceptable salt thereof.

* * * * *